United States Patent
Zhang et al.

(10) Patent No.: US 12,364,677 B2
(45) Date of Patent: Jul. 22, 2025

(54) USE OF CHLOROGENIC ACID IN PREPARATION OF DRUG FOR PREVENTING AND TREATING OCULAR INFLAMMATION

(71) Applicant: SICHUAN JIUZHANG BIOLOGICAL SCIENCE AND TECHNOLOGY CO., LTD, Sichuan (CN)

(72) Inventors: Jie Zhang, Sichuan (CN); Ling Ning, Sichuan (CN); Liang Zhang, Sichuan (CN); Wang Huang, Sichuan (CN)

(73) Assignee: SICHUAN JIUZHANG BIOLOGICAL SCIENCE AND TECHNOLOGY CO., LTD, Sichuan (CN)

( * ) Notice: Subject to any disclaimer, the term of this patent is extended or adjusted under 35 U.S.C. 154(b) by 1078 days.

(21) Appl. No.: 17/425,316

(22) PCT Filed: Dec. 20, 2017

(86) PCT No.: PCT/CN2017/117531
§ 371 (c)(1),
(2) Date: Feb. 7, 2022

(87) PCT Pub. No.: WO2018/133618
PCT Pub. Date: Jul. 26, 2018

(65) Prior Publication Data
US 2022/0184019 A1    Jun. 16, 2022

(30) Foreign Application Priority Data
Jan. 23, 2017 (CN) .......................... 201710051216.4

(51) Int. Cl.
| | | |
|---|---|---|
| *A61K 31/216* | (2006.01) | |
| *A61K 9/00* | (2006.01) | |
| *A61P 27/02* | (2006.01) | |
| *A61P 29/00* | (2006.01) | |

(52) U.S. Cl.
CPC .......... *A61K 31/216* (2013.01); *A61K 9/0019* (2013.01); *A61P 27/02* (2018.01); *A61P 29/00* (2018.01)

(58) Field of Classification Search
CPC .............................. A61K 31/216; A61P 29/00
USPC ......................................................... 514/533
See application file for complete search history.

(56) References Cited

FOREIGN PATENT DOCUMENTS

CN    1813843 A    8/2006

OTHER PUBLICATIONS

USPTO English language translation of CN 1813843 A. (Year: 2006).*

* cited by examiner

*Primary Examiner* — Raymond J Henley, III
(74) *Attorney, Agent, or Firm* — NKL Law; Allen Xue

(57) ABSTRACT

Chlorogenic acid is used in the preparation of a drug for treating and/or preventing ocular inflammation. Chlorogenic acid can significantly alleviate symptoms of uveitis and scleritis, and has good treatment effects on ocular inflammation.

8 Claims, 1 Drawing Sheet

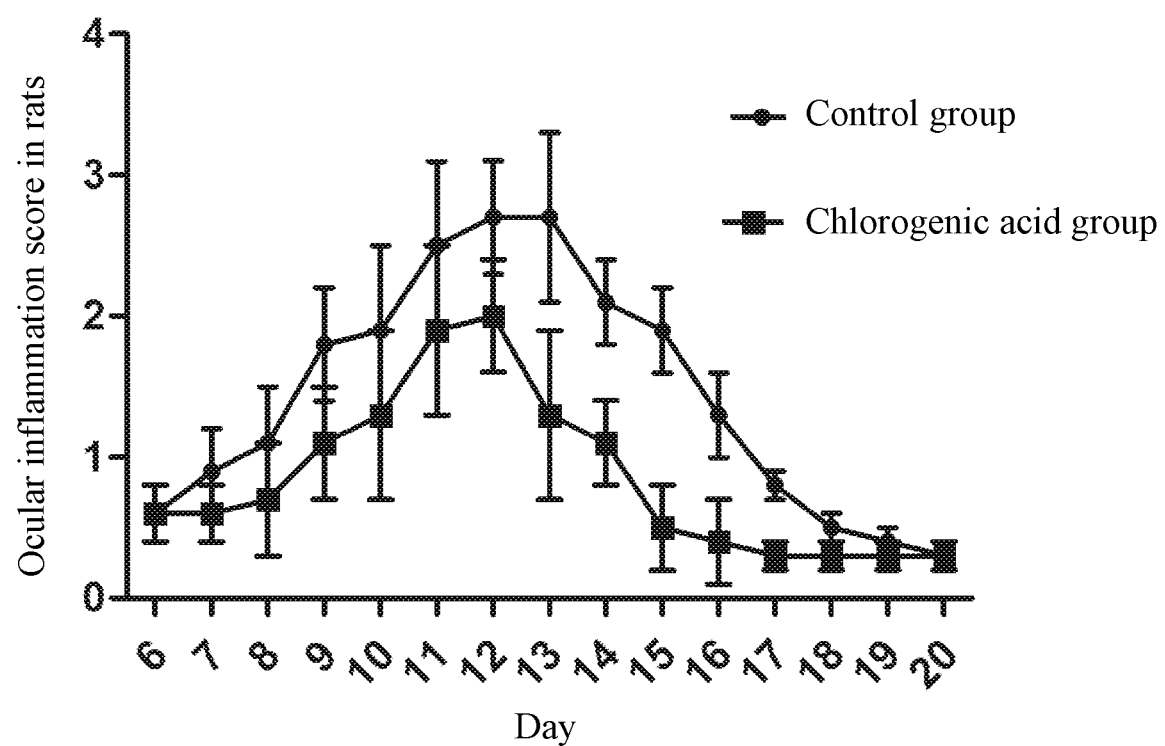

USE OF CHLOROGENIC ACID IN PREPARATION OF DRUG FOR PREVENTING AND TREATING OCULAR INFLAMMATION

TECHNICAL FIELD

The present invention relates to the use of chlorogenic acid in preparation of a drug for prevention and treatment of ocular inflammation, and belongs to the field of medicine.

BACKGROUND ART

Ocular inflammation is an inflammatory reaction of ocular tissues under the influence of external factors and the body's own factors. The clinical morbidity is relatively high, and the more harmful diseases include keratitis, scleritis, uveitis and so on. Keratitis mainly manifests as pain, photophobia, tearing, blepharospasm and other irritation symptoms, as well as ciliary hyperemia, corneal opacity, infiltration or ulcers, etc., and severe cases can cause blindness. Scleritis usually starts with ocular redness and decreased vision, and is characterized by severe eye pain, whose onset is acute and often accompanied by keratitis and uveitis, and the prognosis is poor. Uveitis denotes inflammation of the iris, ciliary body, and choroid occurred at the same time or one after the other. If the inflammation is not treated or treated incorrectly, it can cause complications such as corneal edema, glaucoma, retinal detachment, and so on, and the consequences are very serious. Because the above-mentioned diseases are extremely harmful to eye health, improper treatment can cause blindness, which has attracted worldwide attention.

Therefore, searching for reasonable and effective therapeutic drugs for ocular inflammation has become an urgent problem in the ophthalmology field.

CONTENT OF THE INVENTION

The object of the present invention is to provide the use of chlorogenic acid in the preparation of drugs for preventing and treating ocular inflammation.

The present invention provides the use of chlorogenic acid in preparation of drugs for treatment and/or prevention of ocular inflammation.

Further, the drugs are those for treatment and/or prevention of autoimmune ocular inflammation.

Further, the drugs are those for treatment and/or prevention of uveitis, scleritis, conjunctivitis, keratitis, retinitis, or vitreous inflammation.

Further, the drugs are those for treatment and/or prevention of autoimmune uveitis caused by interphotoreceptor retinoid-binding protein.

Further, the drugs are those for treatment and/or prevention of non-microbial infectious scleritis.

Further, the drug is a preparation obtained by using an effective amount of chlorogenic acid as the active ingredient, with addition of pharmaceutically acceptable excipients or auxiliary ingredients.

Further, the preparation is oral preparations, injections or ophthalmic preparations.

Further, the preparation is intramuscular or intravenous injections.

Further, the injection is prepared from following raw materials at predetermined weight ratios: 30 parts of chlorogenic acid, 2 parts of sodium bisulfite, and 80 parts of mannitol.

Further, each unit of preparation contains 1-500 mg chlorogenic acid.

Further, each unit of preparation contains 210 mg chlorogenic acid.

For administrating to adults, the dosage of chlorogenic acid for injection according to the present invention is 3 mg/kg, based on 70 kg body weight, and so the content of chlorogenic acid in each preparation unit is 210 mg.

The present invention provides a pharmaceutical composition for treating and/or preventing ocular inflammation, which is a preparation prepared by using chlorogenic acid as an active ingredient, with addition of pharmaceutically acceptable excipients or auxiliary ingredients.

The present invention also provides a method for the treatment and/or prevention of ocular inflammation, characterized in that chlorogenic acid is administered to the subject, wherein the subject is a patient with autoimmune ocular inflammation;

wherein the subject is a patient with uveitis, scleritis, conjunctivitis, keratitis, retinitis or vitreous inflammation;

wherein the subject was a patient with autoimmune uveitis caused by an interphotoreceptor retinoid-binding protein;

wherein the subject is a patient with non-infectious scleritis caused by microorganisms.

The present invention provides the use of chlorogenic acid in preparation of drugs for preventing and treating ocular inflammation. Pharmacodynamic experiments show that chlorogenic acid can significantly relieve the symptoms of uveitis and scleritis, and has a good therapeutic effect on ocular inflammation, providing a new choice for clinical medication.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

DESCRIPTION OF FIGURE

FIG. 1 is a graph showing the ocular inflammation scores of the rats in experimental example 1.

EXAMPLES

The starting materials and equipment used in the present invention are all known products and can be obtained by purchasing commercially available products.

Example 1 Preparation of Freeze-Dried Powder Injection of Chlorogenic Acid

In this example, freeze-dried powder injection of chlorogenic acid was prepared according to the method of Example 1 in the patent ZL201310366945.0.

1. Major Drug

Chlorogenic acid, extracted from leaves of *Eucommia ulmoides* Oliv. by Sichuan Jiuzhang Biotechnology Co., Ltd., with a purity of 98.4%.

2. Formula

| Major drug | Chlorogenic acid | 30 g |
|---|---|---|
| Antioxidant | Sodium bisulfite | 2 g |
| Stent agent | Mannitol | 80 g |
| Solvent | Adding water for injection to | 2000 mL |

According to above formula, 1000 freeze-dried powder injections of chlorogenic acid, with a specification of 30 mg/bottle, were prepared by freeze-drying.

In the following experimental examples, the freeze-dried powder injections of chlorogenic acid were all prepared according to Example 1.

In the following, the beneficial effects of the present invention were illustrated by experimental examples.

Experimental Example 1 the Therapeutic Effect of Chlorogenic Acid on Uveitis

Interphotoreceptor retinoid-binding protein (IRBP) was a large molecular glycolipoprotein and the main soluble protein in the interphotoreceptor matrix (IPM). Studies had shown that IRBP could induce experimental autoimmune uveitis (EAU).

1. Establishing Models 6-8 weeks SD rats (30), weighing 160-180 g, are numbered in sequence. The following operations are all carried out in the ultra-clean table: 1 ml PBS was added to one powder of interphotoreceptor retinoid-binding protein (IRBR) (1 mg/bottle), and then mixed well to fully dissolve and obtain the solution of IRBP in PBS at a concentration of 1000 μg/ml, that was stored for later use. 10 mg Mycobacterium tuberculosis H37RA (250 μg*20=5 mg) was weighed under aseptic conditions for use. Two luer lock syringes (5 ml) were connected to the three-way valve, and then 0.6 ml PBS solution containing IRBP, 10 mg Mycobacterium tuberculosis H37RA powder, 1.4 ml PBS, and 2 ml complete Freund's adjuvant (CFA) were sequentially added, respectively. The syringe was repeatedly pushed and drawn to fully emulsify and obtain mixed emulsion (4 ml). The needle was subcutaneously inserted from the middle of the rat's footpad, moved upward to the subcutaneous part of the upper end of the tibia, and 0.2 ml mixed emulsion was slowly injected (the final immunizing dose of each rat was 30 μg IRBP polypeptide and 250 μg Mycobacterium tuberculosis H37RA). The needle was removed, and the injection site was pressed to prevent the emulsion from overflowing. The above operations were repeated to make animal models (30 rats).

2. Administration to Animals

After 6 days of auto-immunization and the appearance of symptoms, the animals were grouped by random number table method and divided into blank control group and chlorogenic acid administration groups, 15 animals for each group, and the drug was intraperitoneally injected. Chlorogenic acid group received the drug at a dose of 20 mg/kg, while the blank control group was intraperitoneally injected with the same dose of normal saline.

3. Observation and Inflammation Scores of Rat Eyes Under a Slit Lamp

The ocular inflammation of each group of rats was observed under a slit lamp every day, and the inflammation score was made with reference to the Caspi clinical grading. The specific scoring criteria were as follows, 0 point: no inflammation, normal red light reflection in the fundus; 0.5 point: mild dilation and hyperemia of iris blood vessels; 1 point: moderate hyperemia of iris blood vessels, miosis; 2 points: mild aqueous turbidity, weakened red light reflection in the fundus; 3 points: moderate aqueous turbidity, weakened red light reflection in the fundus; 4 points: hypopyon, closed pupillary membrane, disappearance of the red light reflection in the fundus.

4. Observation of Ocular Symptoms and Inflammation Score in Rats

The results of inflammation score were shown in Table 1 and FIG. 1.

TABLE 1

Scores of ocular inflammation in rats

| | Time (day) | | | | | | | |
|---|---|---|---|---|---|---|---|---|
| | 6 | 7 | 8 | 9 | 10 | 11 | 12 | 13 |
| Control group | 0.6 ± 0.2 | 0.9 ± 0.2 | 1.1 ± 0.3 | 1.8 ± 0.4 | 1.9 ± 0.4 | 2.5 ± 0.8 | 2.7 ± 0.6 | 2.7 ± 0.6 |
| Chlorogenic acid group | 0.6 ± 0.2 | 0.6 ± 0.2 | 0.7 ± 0.4 | 1.1 ± 0.4 | 1.3 ± 0.6 | 1.9 ± 0.6 | 2.0 ± 0.4 | 1.3 ± 0.6 |

| | Time (day) | | | | | | |
|---|---|---|---|---|---|---|---|
| | 14 | 15 | 16 | 17 | 18 | 19 | 20 |
| Control group | 2.1 ± 0.4 | 1.9 ± 0.4 | 1.3 ± 0.4 | 0.8 ± 0.4 | 0.5 ± 0.3 | 0.4 ± 0.3 | 0.3 ± 0.3 |
| Chlorogenic acid group | 1.1 ± 0.3 | 0.5 ± 0.3 | 0.4 ± 0.3 | 0.3 ± 0.1 | 0.3 ± 0.1 | 0.3 ± 0.1 | 0.3 ± 0.1 |

Experimental results: the control group showed iris blood vessel congestion and pupils narrow. After that, the ocular symptoms aggravated as the number of days of immunization increased. On the 9th day after immunization, the symptoms were obvious and manifested as iris vascular congestion, hypopyon and pyogenic posterior chamber, pupillary exudation, and weakened red light reflection in the fundus. Symptoms reached the peak on the 12th day of immunization, and were shown as anterior aqueous turbidity and empyema, part of closed pupil membrane, anterior chamber shallowing, bulged iris, and even hemorrhage from the anterior chamber, as well as almost disappearance of red light reflection in the fundus. Then, the symptoms gradually relieved. After 15 days of immunization, except that the pupils of some rats were still closed, most of the pupils were open, the empyema in anterior chamber and posterior chamber decreased, the exudation was initially absorbed, the anterior chamber deepened, and the iris blood vessels were congested. On the 20th day of immunization, the rats' symptoms were further relieved, the closed pupil membrane disappeared, the depth of anterior chamber was basically normal, the aqueous humor was slightly turbid, the iris blood vessels were congested, and the red light reflection in the fundus was present.

Compared with the control group, the ocular inflammation of rats in the chlorogenic acid treatment group was significantly reduced at the same time point. On the 9th day after immunization, the ocular symptoms were mild, and included turbid anterior aqueous humor, iris blood vessel congestion, blurred texture, and abnormally reduced pupils. On the 12th day, the iris vascular congestion progressed, together with the moderate turbidity of anterior aqueous humor, and then the symptoms quickly relieved. On the 15th day after immunization, pupils were basically normal, anterior chamber depth was also basically normal, and aqueous humor was clear or slightly turbid.

From the 6th day after immunization, the ocular inflammation score of the rats in the chlorogenic acid treatment group was significantly lower than that in the control group at the same time point ($P<0.05$).

The above results indicated that chlorogenic acid had a significant therapeutic effect on uveitis.

Experimental Example 2 Clinical Efficacy and Results of Chlorogenic Acid on Scleritis Twenty patients with scleritis were randomly divided into chlorogenic acid test group (10 patients) and control group (10 patients). Patients in chlorogenic acid test group were given chlorogenic acid at a dose of 3 mg/(kg·d) by intramuscular injection. The patients in the control group were given dexamethasone sodium phosphate (5 mg/d) by intravenous injection, and after continuous observation and treatment for 5 days, they initially received oral precision (1 mg/(kg·d)). Both groups were continuously administrated for one month.

1. General Clinical Data

Phase I clinical trial (clinical batch number: 2013L01855) of chlorogenic acid for injection for the treatment of malignant glioma has been carried out in Beijing Shijitan Hospital affiliated to Capital Medical University. In this trial, all subjects were intramuscularly injected the freeze-dried powder of chlorogenic acid every morning at the dosage of their respective group.

According to the random table, 20 patients with scleritis were randomly divided into two groups, namely chlorogenic acid test group and dexamethasone sodium phosphate control group. Among 10 patients of chlorogenic acid control group, there were one male and 9 females, with an average age of (30.5±5.1) years old and an average course of disease (5.1±0.3). In the dexamethasone sodium phosphate control group, there were one male and 9 females, with an average age of (31.5±4.7) years old and an average course of disease (5.5±0.3). For both groups of patients, there was no statistically significant difference ($P>0.05$) in the clinical data including age, gender, and disease course, having comparability.

2. Inclusion Criteria:

(1) Inquiring the medical history in detail, performing detailed examinations such as slit lamp examination, fundus examination, ultrasound examination, eye imaging, etc., and making a clear diagnosis of the patient with scleritis; (2) No glucocorticoid and chlorogenic acid contraindications; (3) Patients having non-microbial infectious scleritis; (4) Patients having no obvious abnormalities in blood routine, electrolytes, liver function, kidney function, blood pressure, blood sugar, and so on.

3. Exclusion Criteria:

(1) Patients with microbial infectious scleritis and systemic infectious diseases; (2) Episcleritis; (3) Patients allergic to glucocorticoids or having toxic side effects due to administration of glucocorticoids; (4) Pregnant women and lactating women as well as babies; (5) Patients with moderate hypertension, severe cardiovascular and cerebrovascular diseases, diabetes, as well as liver and kidney function impairment; (6) Patients having poor compliance and refusing regular review and follow-up.

4. Treatment Method:

Patients in chlorogenic acid test group were given chlorogenic acid at a dose of 3 mg/(kg·d) by intramuscular injection. The patients in the control group were given dexamethasone sodium phosphate at 5 mg/day by intravenous infusion, and after continuous observation and treatment for 3 days, they were changed to oral prednison (1 mg/(kg·d)). Both groups were continuously administrated for one month.

5. Evaluation Criteria of Therapeutic Effect:

(1) Cure: the eye symptoms and signs completely disappeared after treatment; (2) Improved: the eye symptoms and signs improved after treatment; (3) Ineffective: the inflammation was not controlled, or the situation was the same as before treatment.

6. Evaluation Standard of Visual Acuity:

(1) After treatment, the same logarithmic visual acuity chart (the best corrected visual acuity was measured for those with ametropia) was used to detect and record the vision. Significant improvement: improving 3 lines or more; improvement: improving 1-2 lines; ineffective: the vision was not improved or even decreased.

7. Results:

TABLE 2

Clinical effect of chlorogenic acid on scleritis (inflammation control in one month)

| Group | n (cases) | Cure | Improved | Ineffective | Total effective rate |
|---|---|---|---|---|---|
| Chlorogenic acid group | 10 | 5 (50%)* | 3 (30%) | 2 (20%) | 8 (80%)* |
| Control group | 10 | 2 (20%) | 3 (30%) | 5 (50%) | 5 (50%) |

Note:
comparison between two groups,
*P < 0.05

TABLE 3

Vision recovery in one month

| Group | n (case) | Significantly improved vision | Improved | Ineffective | Total effective rate |
|---|---|---|---|---|---|
| Chlorogenic acid group | 10 | 6 (60%)* | 3 (30%) | 1 (10%) | 90 (90%)* |
| Control group | 10 | 3 (30%) | 3 (30%) | 4 (40%) | 60 (60%) |

Note:
comparison between two groups,

TABLE 3-continued

Vision recovery in one month

| Group | n (case) | Significantly improved vision | Improved | Ineffective | Total effective rate |
|---|---|---|---|---|---|

*P < 0.05

Experimental results: Chlorogenic acid group was significantly better than the control group in terms of inflammation control effect and vision recovery (P<0.05), indicating that chlorogenic acid could effectively treat scleritis.

The invention claimed is:

1. A method for the treatment ocular inflammation, comprising:
    administrating a drug preparation comprising an effective amount of chlorogenic acid to a subject in need thereof, wherein the ocular inflammation is uveitis, scleritis, keratitis, retinitis, or vitreous inflammation.

2. The method according to claim 1, wherein the uveitis is autoimmune uveitis caused by an interphotoreceptor retinoid-binding protein.

3. The method according to claim 1, wherein the scleritis is a non-infectious scleritis caused by microorganisms.

4. The method according to claim 1, wherein the drug preparation further comprises a pharmaceutically acceptable excipient.

5. The method according to claim 1, wherein the drug preparation is administered as an oral preparations, an injection, or an ophthalmic preparation.

6. The method according to claim 1, wherein the drug preparation is administered by intramuscular or intravenous injection.

7. The method according to claim 1, wherein the drug preparation comprises, by weight, 30 parts of chlorogenic acid, 2 parts of sodium bisulfite, and 80 parts of mannitol.

8. The method according to claim 5, wherein the drug preparation is administered in a unit that contains 1-500 mg chlorogenic acid.

* * * * *